(12) United States Patent
Gray

(10) Patent No.: US 6,234,961 B1
(45) Date of Patent: May 22, 2001

(54) BALL AND SOCKET INTERCONNECTION AND RETRACTOR ASSEMBLY EMPLOYING THE SAME

(75) Inventor: Bruce Nathaniel Gray, Claremont (AU)

(73) Assignee: Pineridge Holding Pty. Ltd. (AU)

( * ) Notice: Subject to any disclaimer, the term of this patent is extended or adjusted under 35 U.S.C. 154(b) by 0 days.

(21) Appl. No.: 09/292,512

(22) Filed: Apr. 15, 1999

(30) Foreign Application Priority Data

Apr. 15, 1998 (AU) .................................................. PP2946

(51) Int. Cl.⁷ ..................................................... A61B 1/32
(52) U.S. Cl. ........................................... 600/234; 403/122
(58) Field of Search ................................... 600/227, 228, 600/229, 234; 403/122, 124, 125, 126, 142

(56) References Cited

U.S. PATENT DOCUMENTS

| 2,623,517 | * | 12/1952 | Barlow et al. | 600/234 X |
|---|---|---|---|---|
| 3,002,466 | | 10/1961 | Read . | |
| 3,003,399 | * | 10/1961 | Donner | 403/122 X |
| 3,586,358 | | 6/1971 | Kiesow | 287/88 |
| 3,871,782 | | 3/1975 | Johansson et al. | 403/122 |
| 4,411,545 | | 10/1983 | Roberge | 403/12 |
| 4,697,993 | | 10/1987 | Chamberlin et al. | 417/514 |
| 4,917,527 | | 4/1990 | Bollinger | 403/90 |
| 5,074,699 | | 12/1991 | Blaisdell et al. | 403/122 |
| 5,114,261 | | 5/1992 | Sugimoto et al. | 403/122 |

FOREIGN PATENT DOCUMENTS

| 2233561 | * | 8/1974 | (GB) | 600/234 |
|---|---|---|---|---|
| 2307641 | * | 8/1974 | (DE) | 403/122 |
| WO97/40752 | | 4/1997 | (WO) . | |

* cited by examiner

Primary Examiner—Jeffrey A. Smith
(74) Attorney, Agent, or Firm—Needle & Rosenberg, P.C.

(57) ABSTRACT

A ball and socket interconnection capable of use in surgical retractor systems comprising a ball member and a socket member, the socket member defining an entry and being adapted to releasably receive the ball member such that when the ball member is received in the socket member it is capable of pivotal and rotational movement within the socket, the ball member having two spherical end surfaces between which is located an intermediate section, the spherical end surfaces having a radius of curvature greater than the radius of curvature of the entry and the intermediate section having a radius of curvature less than the radius of curvature of the entry, whereby the intermediate section renders the ball member releasably receivable in the socket member.

18 Claims, 3 Drawing Sheets

BALL AND SOCKET INTERCONNECTION AND RETRACTOR ASSEMBLY EMPLOYING THE SAME

FIELD OF THE INVENTION

This invention relates to a ball and socket interconnection. More particularly, this invention relates to a ball and socket interconnection that can be easily assembled and separated and when assembled is capable substantial pivotal and rotational movement. The present invention also relates to a surgical retractor assembly employing the ball and socket interconnection.

BACKGROUND ART

Ball and socket joints have many applications and are used for connecting two components in a way that allows for relative movement between the components.

Existing ball and socket joints suffer from a number of problems insofar as they may not permit sufficient movement between the connected components for all applications. Furthermore, prior art joints are not generally separated easily because the ball and socket elements are either permanently held together or held together in such a way that it is difficult to separate them without the use of other tools. Finally and in general prior art joints are not conveniently and releasably lockable.

Surgical retractors are used to hold apart tissues or organs that overlie the organ(s) of interest during surgical procedures. A surgical retractor consists of a rigid frame to which retractor blades are attached. The retractor blades are placed in a desired position and fixed into that position in order to hold open tissue or organ(s) during surgical operations. The rigid frame may consist of different shapes including rings, ovals and independent arms. For greater stability the rigid frame is often fixed to the operating table by a table mounted clamping assembly.

Whilst ball and socket joints have been used to connect components of surgical retractor systems, they currently provide limited movement between components and are complicated to separate. Furthermore, prior art ball and socket joints do not provide a convenient means for releasably locking the components in a fixed position.

The present invention seeks to provide a ball and socket interconnection that is simple to separate and assemble and when assembled allows for substantial relative movement.

The present invention also seeks to provide a lockable ball and socket interconnection that is simple to separate and assemble and when assembled allows for substantial relative movement.

DISCLOSURE OF THE INVENTION

The present invention provides a ball and socket interconnection comprising a ball member and a socket member, the socket member defining an entry and being adapted to releasably receive the ball member such that when the ball member is received in the socket member it is capable of pivotal and rotational movement within the socket, the ball member having two spherical end surfaces between which is located an intermediate section, the spherical end surfaces having a radius of curvature greater than the radius of curvature of the entry and the intermediate section having a radius of curvature less than the radius of curvature of the entry, whereby the intermediate section renders the ball member releasably receivable in the socket member.

The ball member may be varied provided it is receivable in the socket member and capable of pivotal and rotational movement whilst received therein. The relative radii of the end surfaces of the ball member, the intermediate section and the entry of the socket member are important in the functioning of the invention and will be discussed in more detail below.

The intermediate section may vary provided it has a smaller radius of curvature than the end surfaces and the entry. Preferably, the intermediate section comprises an annular ring that defines a rebate on the surface of the ball member. Alternatively, the intermediate section may comprise a cylinder that provides the reduced radius.

The intermediate section may also comprise a cross member with a substantially reduced radius of curvature relative to the end surfaces and the entry. In this form, the intermediate section may be a shaft or spindle extending between the end surfaces. It will be appreciated that the surface profile of the intermediate section is of no importance, its purpose is to allow for the ball member to be receivable in the socket member.

The end surfaces of the ball member may be varied provided they are compatible with the socket member to be rotatable and pivotal when the ball member is received therein. Preferably, the outer surface of the end surfaces is uniform and smooth and the relative radii of the end surfaces and the socket member is such that there is limited lateral movement between them when the ball member is received in the socket member.

The socket member may be varied provided it is compatible with the ball member. Preferably, the entry has a radius that is only slightly reduced relative to that of the socket member. In one particular form the radius of the socket member is adjustable thus allowing the ball member and socket member to be locked in position.

Thus, the present invention also provides a lockable ball and socket interconnection comprising a ball member and an adjustable socket member, the adjustable socket member being adapted to releasably lock the ball and socket interconnection, and defining an entry and being adapted to releasably receive the ball member such that when the ball member is received in the socket member it is capable of pivotal and rotational movement within the socket, the ball member having two spherical end surfaces between which is located an intermediate section, the spherical end surfaces having a radius of curvature greater than the radius of curvature of the entry and the intermediate section having a radius of curvature less than the radius of curvature of the entry, whereby the intermediate section renders the ball member releasably receivable in the socket member.

The adjustable socket member may be varied provided it is adapted to lock the interconnection. Preferably, the adjustable socket member comprises a clamp member within which is defined a socket for receiving the ball member. Preferably, the clamp member is a U clamp comprising an actuating member and the socket is defined within the arms of the U clamp such that operation of the clamp via the actuating member adjusts the size of the socket.

Preferably, the actuating member is a handle operably connected to a bolt member that passes through the arms of the U clamp to mate with an abutments member such as a nut on the side of the clamp opposed to the handle.

In one particular form, the handle is pivotally mounted and further comprises a cam that allows for the adjustment of the U clamp through pivotal movement of the handle. The cam adjustment allows for convenient release and locking of the interconnection.

The ball and socket interconnection of the present invention has particular application in surgical retractor systems.

Thus, the present invention also provides a surgical retractor system comprising a lockable ball and socket interconnection comprising a ball member and an adjustable socket member, the adjustable socket member being adapted to releasably lock the ball and socket interconnection, and defining an entry and being adapted to releasably receive the ball member such that when the ball member is received in the socket member it is capable of pivotal and rotational movement within the socket, the ball member having two spherical end surfaces between which is located an intermediate section, the spherical end surfaces having a radius of curvature greater than the radius of curvature of the entry and the intermediate section having a radius of curvature less than the radius of curvature of the entry, whereby the intermediate section renders the ball member releasably receivable in the socket member.

When used as part of a surgical retractor system either or both of the ball and socket members may be provided integrally with a part of the retractor system. Preferably, the ball member is provided integrally with a ring, wishbone or support arm used in the system and from which other instruments such as retractor blades are supported.

The present invention will now be described with reference to the accompanying figures, which illustrate one preferred embodiment of the present invention. The description of the figures in no way limits the generality of the preceding paragraphs.

BEST MODE(S) FOR CARRYING OUT THE INVENTION

Figure 1:
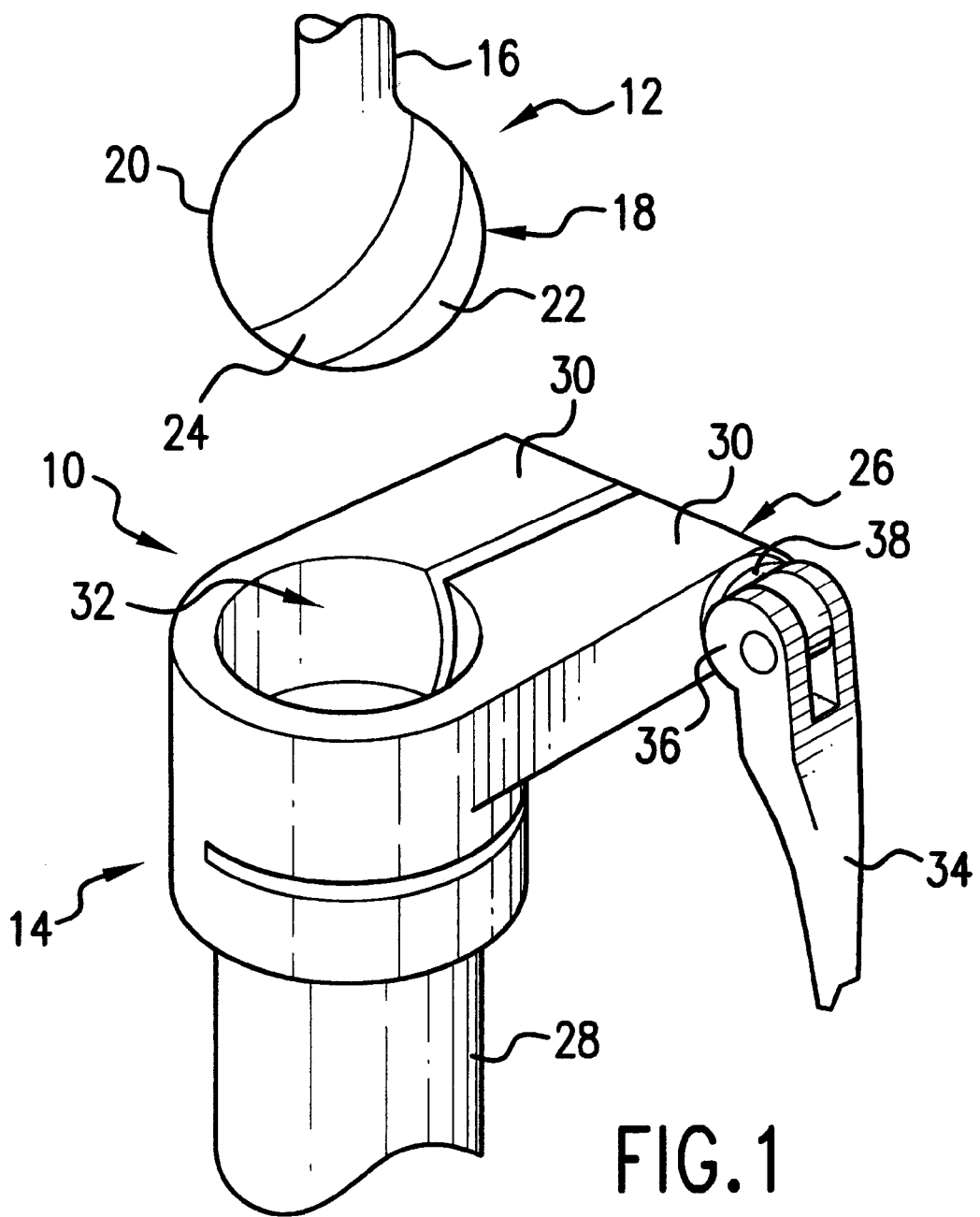
FIG. 1 is a detailed perspective view of an ball and socket interconnection according to a preferred embodiment of the present invention.

The interconnection depicted in the figures is generally indicated by the numeral 10 and includes a ball member 12 and a socket member 14. The ball member 12 includes a shaft portion 16 via which the ball member 12 may be operably connected to another piece of equipment, and a ball portion 18 adapted to be releasably received in the socket member 14 so as to be capable of rotational and pivotal movement. The ball portion 18 has two spherical end surfaces 20, 22 and an intermediate section therebetween in the form of a cylinder that defines an annular rebate 24 on the surface of the ball portion 18.

The socket member 14 comprises a U clamp 26 mounted on a shaft 28. The arms 30 of the U clamp 26 define a generally spherical inner space adapted to receive the ball portion 16 of the ball member 12. The radius of the inner space is greater than that of the end surfaces 20, 22 so as to be compatible with the ball portion 18. The arms 30 of the U clamp 26 also define a generally circular entry 32 with a radius less than the radius of the inner space. The radius of curvature of the cylinder which defines the annular rebate 24 is less than the radius of curvature of the entry 32 and the radius of curvature of the end surfaces 20, 22 is greater than the radius of curvature of the entry 32. These relative radii enable the ball portion 18 to be releasably received in the socket member 14 and to be capable of rotational and pivotal movement when so received.

The radius of the inner space defined by the U clamp 26 may be adjusted by operation of the U clamp 26. The U clamp 26 may be opened or closed as required by rotating or pivoting the handle 34 which is operably connected to a bolt (not shown) which passes through compatible bores in the upper portions of the arms 30 to mate with a nut (not shown) at the end of the bolt remote from the handle 34. Rotation of the handle 34 causes the arms 30 to open or close thereby adjusting the radius of the inner space of the socket member 14.

The pivotal movement of the handle 34 also adjusts the radius of the inner space through the action of a cam 36 on the handle 34. Pivotal movement of the handle 34 rotates the cam 36 which in turn abuts on spacer 38 and actuates the bolt to open or close the arms 30 and thus control the size of the inner space without rotating the handle 34.

Figure 2:
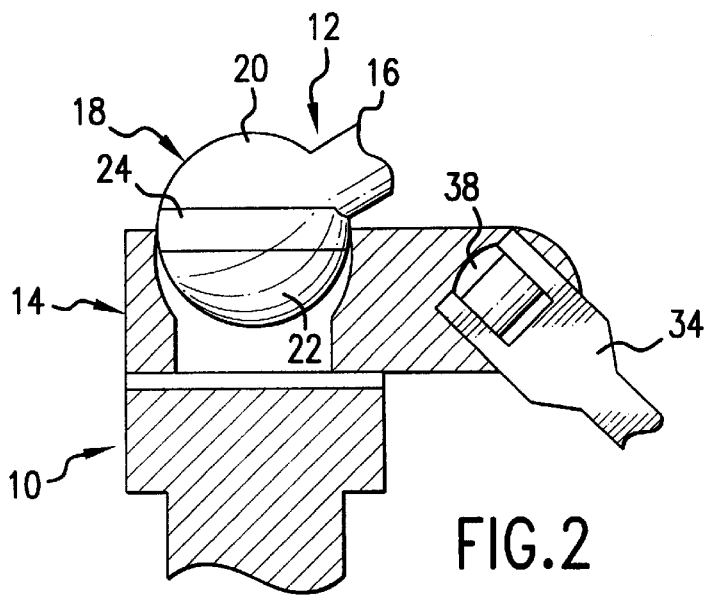
FIGS. 2 and 3 illustrate the operation of the interconnection of FIG. 1, the socket member of the interconnection is shown in cross-section to better demonstrate the interaction between the ball and socket portion.
Figure 3:
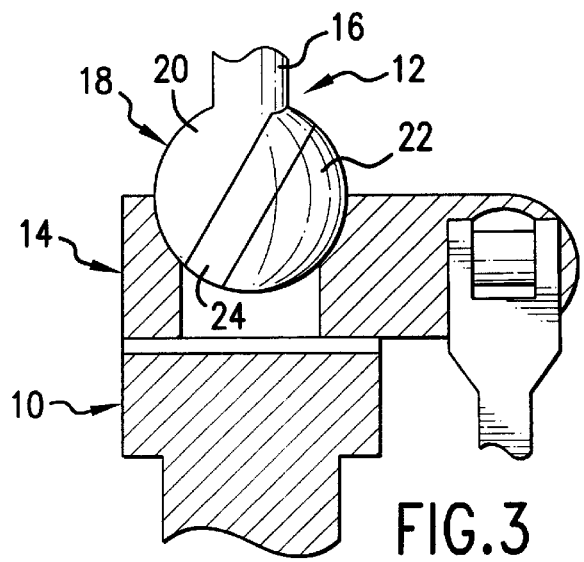

FIGS. 2 and 3 depict the insertion of the ball member 12 in the socket member 14. When the annular rebate 24 is presented substantially parallel to the entry 26 the ball portion 18 can pass through the entry 32 and thus be inserted into the socket member 14. Once inserted, rotation of the ball member 12 brings the perimeter of the entry 32 into abutting relationship with the end surfaces 20, 22 thus releasably retaining the ball member 12 in the socket member 14 and allowing the ball member to be rotatable about multiple axis whilst retained in the socket member 14. Once in the desired position, the ball member 12 may be fixed in position through operation of the handle 34 to decrease the radius of the inner space of the socket member 14 such that it abuts the ball member 14.

Figure 4:
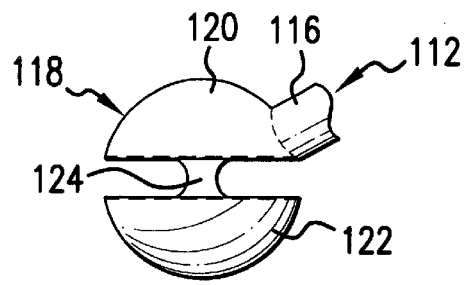
FIG. 4 depicts an alternative ball member to that depicted in FIG. 1.

FIG. 4 illustrates an alternative ball member generally indicated by the numeral 112 which is an alternative to the ball member depicted in FIG. 1 in the interconnection of the present invention. The ball member 112 includes a shaft portion 116 via which the ball member 112 may be operably connected to another piece of equipment, and a ball portion 118. The ball portion 118 has two spherical end surfaces 120, 122 and an intermediate section therebetween in the form of a shaft 124.

Figure 5:
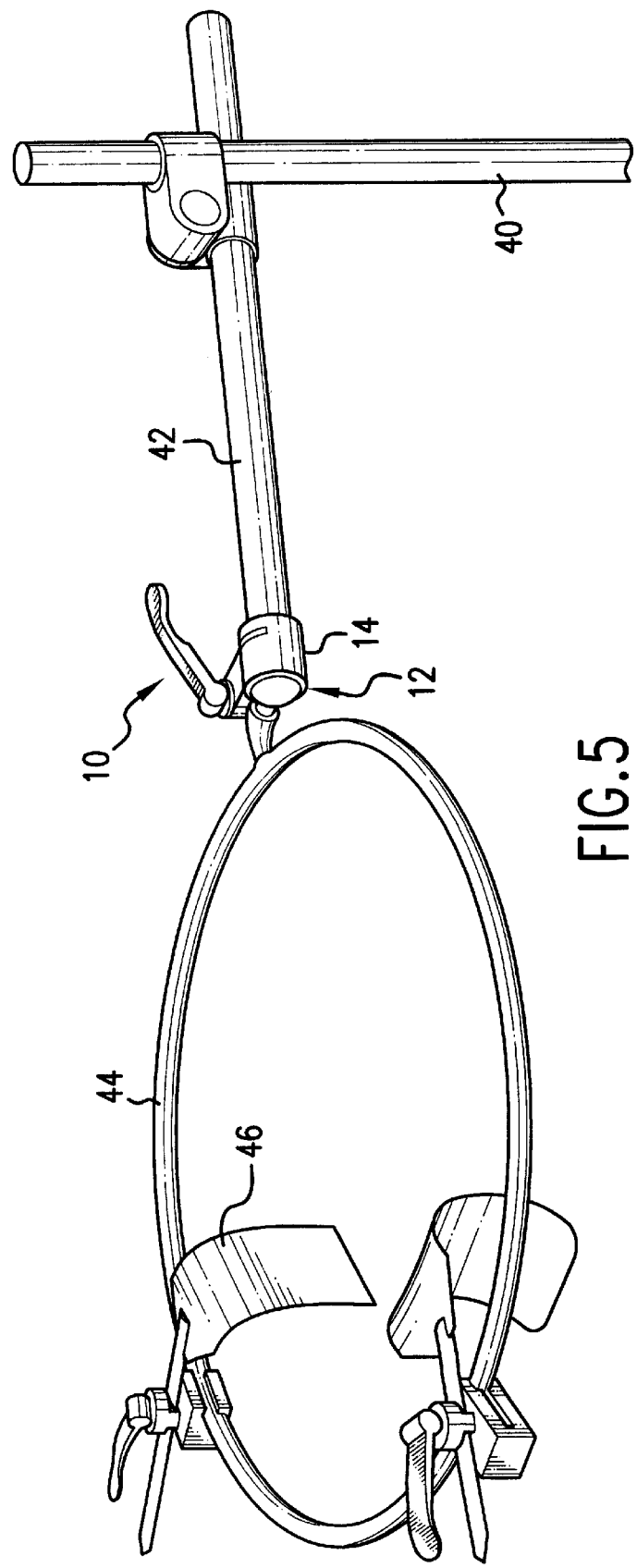
FIG. 5 depicts a surgical retractor system employing the interconnection of FIG. 1.

FIG. 5 depicts a surgical retractor system employing the interconnection of FIG. 1. The surgical retractor system includes a vertical stand 40 releasably mounted on which is a cross-bar 42. The cross-bar 42 is moveable up and down the stand 40, as required, and supports a ring 44 at its end remote from the stand 40 via a ball and socket interconnection 10. The ring 44 serves as a support for other surgical instruments such as blades 46.

In the system depicted in FIG. 5, the ball member 12 is provided integrally with the ring 44. The inclusion of the ball and socket interconnection 10 in the system allows for any size ring 44 to be used in the system and for simple and efficient interchange of rings. The ring 44 may of course be substituted with an independent arm or any other attachment capable of supporting other surgical instruments. Furthermore, the rotational and pivotal movement imparted on the system by the interconnection 10 allows the ring 44 to be positioned in various positions, as required.

Further modifications apparent to one skilled in the art are encompassed by the present invention. Furthermore, throughout the specification, unless the context requires otherwise, the word "comprise" or variations such as "comprises" or "comprising", will be understood to imply the inclusion of a stated integer or group of integers but not the exclusion of any other integer or group of integers.

What is claimed is:

1. A lockable ball and socket interconnection comprising a ball member and an adjustable socket member, the adjustable socket member defining an entry and being adapted to releasably receive the ball member such that when the ball member is received in the socket member it is capable of pivotal and rotational movement within the socket, the ball member having two spherical end surfaces between which is located an intermediate section, the spherical end surfaces having a radius of curvature greater than the radius of curvature of the entry and the intermediate section having a radius of curvature less than the radius of curvature of the entry, wherein the intermediate section renders the ball member releasably receivable in the socket member, and wherein the adjustable socket member is adapted to releasably lock the ball and socket interconnection such that the ball member and the socket member may be releasably fixed in relative position to each other.

2. The lockable ball and socket interconnection according to claim 1 wherein the intermediate section comprises an annular ring that defines a rebate on the surface of the ball member.

3. The lockable ball and socket interconnection according to claim 1 wherein the intermediate section comprises a cylinder.

4. The lockable ball and socket interconnection according to claim 1 wherein the intermediate section comprises a cross member with a substantially reduced radius of curvature relative to the end surfaces and the entry.

5. The lockable ball and socket interconnection according to claim 4 wherein the cross member comprises a shaft or spindle extending between the end surfaces.

6. The lockable ball and socket interconnection according to claim 1 wherein the outer surface of the end surfaces is uniform and smooth and the relative radii of the end surfaces and the socket member is such that there is limited lateral movement between them when the ball member is received in the socket member.

7. The lockable ball and socket interconnection according to claim 1 wherein the entry has a radius that is only slightly reduced relative to that of the socket member.

8. A lockable ball and socket interconnection comprising a ball member and an adjustable socket member, wherein the adjustable socket member comprises a clamp member, the clamp member being adapted to releasably lock the ball and socket interconnection, and defining an entry and being adapted to releasably receive the ball member such that when the ball member is received in the socket member it is capable of pivotal and rotational movement within the socket, the ball member having two spherical end surfaces between which is located an intermediate section, the spherical end surfaces having a radius of curvature greater than the radius of curvature of the entry and the intermediate section having a radius of curvature less than the radius of curvature of the entry, whereby the intermediate section renders the ball member releasably receivable in the socket member.

9. The lockable ball and socket interconnection according to claim 8 wherein the clamp member comprises an actuating member and two opposed arms and the socket is defined between the arms of the clamp member such that operation of the clamp member via the actuating member adjusts the size of the socket member.

10. The lockable ball and socket interconnection according to claim 9 wherein the actuating member is a handle operably connected to a bolt member that passes through the arms of the clamp member to mate with an abutment member on the side of the clamp member opposed to the handle.

11. The lockable ball and socket interconnection according to claim 10 wherein the handle is pivotally mounted and further comprises a cam that allows for the adjustment of the clamp member through pivotal movement of the handle.

12. The lockable ball and socket interconnection according to claim 8 wherein the clamp member is a U shaped clamp.

13. A surgical retractor system including a lockable ball and socket interconnection comprising a ball member and an adjustable socket member, the adjustable socket member being adapted to releasably lock the ball and socket interconnection, and defining an entry and being adapted to releasably receive the ball member such that when the ball member is received in the socket member it is capable of pivotal and rotational movement within the socket, the ball member having two spherical end surfaces between which is located an intermediate section, the spherical end surfaces having a radius of curvature greater than the radius of curvature of the entry and the intermediate section having a radius of curvature less than the radius of curvature of the entry, whereby the intermediate section renders the ball member releasably receivable in the socket member.

14. The surgical retractor system according to claim 13 wherein either or both of the ball and socket members are provided integrally with another part of the retractor system.

15. The surgical retractor system according to claim 14 wherein the ball member is provided integrally with a ring, wishbone or support arm.

16. A surgical retractor system including a lockable ball and socket interconnection comprising a ball member and an adjustable socket member, wherein the adjustable socket member comprises a clamp member, the clamp member being adapted to releasably lock the ball and socket interconnection, and defining an entry and being adapted to releasably receive the ball member such that when the ball member is received in the socket member it is capable of pivotal and rotational movement within the socket, the ball member having two spherical end surfaces between which is located an intermediate section, the spherical end surfaces having a radius of curvature greater than the radius of curvature of the entry and the intermediate section having a radius of curvature less than the radius of curvature of the entry, whereby the intermediate section renders the ball member releasably receivable in the socket member.

17. The surgical retractor system according to claim 16 wherein either or both of the ball and socket members are provided integrally with another part of the retractor system.

18. The surgical retractor system according to claim 17 wherein the ball member is provided integrally with a ring, wishbone or support arm.

* * * * *